US008277826B2

(12) United States Patent
Krongauz et al.

(10) Patent No.: US 8,277,826 B2
(45) Date of Patent: Oct. 2, 2012

(54) METHODS FOR MAKING ANTIMICROBIAL RESINS

(75) Inventors: Vadim V. Krongauz, Bartlett, IL (US); Dustin C. Cawthon, Crystal Lake, IL (US); Michael Tung-Kiung Ling, Vernon Hills, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 752 days.

(21) Appl. No.: 12/145,548

(22) Filed: Jun. 25, 2008

(65) Prior Publication Data
US 2009/0324666 A1 Dec. 31, 2009

(51) Int. Cl.
*A01N 25/08* (2006.01)
(52) U.S. Cl. ........................................................ 424/409
(58) Field of Classification Search .................. 424/409
See application file for complete search history.

(56) References Cited

U.S. PATENT DOCUMENTS

| | | | |
|---|---|---|---|
| 1,610,391 A | 12/1926 | Smith | |
| 1,783,334 A | 12/1930 | Keelan | |
| 3,856,805 A | 12/1974 | Margraf | |
| 3,932,627 A | 1/1976 | Margraf | |
| 4,045,400 A | 8/1977 | Korshak et al. | |
| 4,412,834 A | 11/1983 | Kulin et al. | |
| 4,417,890 A | 11/1983 | Dennehey et al. | |
| 4,440,207 A | 4/1984 | Genatempo et al. | |
| 4,457,749 A | 7/1984 | Bellotti et al. | |
| 4,485,064 A | 11/1984 | Laurin | |
| 4,581,028 A | 4/1986 | Fox, Jr. et al. | |
| 4,592,920 A | 6/1986 | Murtfeldt | |
| 4,603,152 A | 7/1986 | Laurin et al. | |
| 4,632,844 A | 12/1986 | Yanagihara et al. | |
| 4,738,668 A | 4/1988 | Bellotti et al. | |
| 4,990,363 A | 2/1991 | Suhr et al. | |
| 5,019,096 A | 5/1991 | Fox, Jr. et al. | |
| 5,236,703 A | 8/1993 | Usala | |
| 5,242,532 A | 9/1993 | Cain | |
| 5,360,413 A | 11/1994 | Leason et al. | |
| 5,614,568 A | 3/1997 | Mawatari et al. | |
| 5,616,338 A | 4/1997 | Fox, Jr. et al. | |
| 5,630,804 A | 5/1997 | Imada et al. | |
| 5,643,190 A * | 7/1997 | Utterberg | 604/6.15 |
| 5,718,694 A | 2/1998 | Rupp | |
| 5,730,418 A | 3/1998 | Feith et al. | |
| 5,744,151 A | 4/1998 | Capelli | |
| 5,782,816 A | 7/1998 | Werschmidt et al. | |
| 5,863,548 A | 1/1999 | Elder | |
| 5,928,174 A | 7/1999 | Gibbins | |
| 5,948,385 A | 9/1999 | Chapman et al. | |
| 6,030,632 A | 2/2000 | Sawan et al. | |
| 6,039,302 A | 3/2000 | Cote, Sr. et al. | |
| 6,103,868 A | 8/2000 | Heath et al. | |
| 6,106,505 A | 8/2000 | Modak et al. | |
| 6,113,636 A | 9/2000 | Ogle | |
| 6,126,931 A | 10/2000 | Sawan et al. | |
| 6,150,430 A | 11/2000 | Walters et al. | |
| 6,180,584 B1 | 1/2001 | Sawan et al. | |
| 6,246,824 B1 | 6/2001 | Vandeberg et al. | |
| 6,264,936 B1 | 7/2001 | Sawan et al. | |
| 6,265,476 B1 | 7/2001 | Krongauz et al. | |
| 6,267,782 B1 | 7/2001 | Ogle et al. | |
| 6,323,256 B1 | 11/2001 | DelMain | |
| 6,329,488 B1 | 12/2001 | Terry et al. | |
| 6,355,858 B1 | 3/2002 | Gibbins | |
| 6,443,980 B1 * | 9/2002 | Wang et al. | 623/1.11 |
| 6,465,167 B2 | 10/2002 | Whitcomb et al. | |
| 6,472,451 B2 | 10/2002 | Ha et al. | |
| 6,480,250 B1 | 11/2002 | Matsufuji et al. | |
| 6,497,901 B1 | 12/2002 | Royer | |
| 6,506,293 B1 | 1/2003 | Rumpf | |
| 6,506,814 B2 | 1/2003 | Krongauz et al. | |
| 6,530,951 B1 | 3/2003 | Bates et al. | |
| 6,548,121 B1 | 4/2003 | Bauer et al. | |
| 6,565,913 B2 | 5/2003 | Arps et al. | |
| 6,579,539 B2 | 6/2003 | Lawson et al. | |
| 6,592,814 B2 | 7/2003 | Wilcox et al. | |
| 6,596,401 B1 | 7/2003 | Terry et al. | |

(Continued)

FOREIGN PATENT DOCUMENTS

CN 18734048 12/2006

(Continued)

OTHER PUBLICATIONS

Lok et al., Silver nanoparticles: partial oxidation and antibacterial activities, J. Biol. Inorg. Chem., 12:527-34 (2007).
Final office action from U.S. Appl. No. 12/164,414, dated Feb. 25, 2011.
Final office action from U.S. Appl. No. 12/143,304, dated Mar. 8, 2011.
Schwartz, Encyclopedia of Materials, Parts, and Finishes, Second Edition, p. 857, CRC Press (2002).
Tang et al., Studies on measurement of chloride ion concentration in concrete structures with long-period grating sensors, in: Tomizuka et al. (eds.), Smart Structures and Materials 2006, Proc. of SPIE, vol. 6174, 11 pages (2006).
Kim et al., Antimicrobial effects of silver nanoparticles, *Nanomed.: Nanotechnol. Biol. Med.*, 3:95-101 (2007).
Copending U.S. Appl. No. 12/400,439 (Carter et al.), filed Mar. 9, 2009.
Elliott et al., Intravascular catheter-related sepsis—novel methods of prevention, *Intensive Care Med.*, 26:S45-50 (2000).

(Continued)

*Primary Examiner* — Richard Schnizer
*Assistant Examiner* — Audrea Buckley
(74) *Attorney, Agent, or Firm* — Marshall, Gerstein & Borun LLP

(57) ABSTRACT

Methods for making antimicrobial resins and for forming coatings comprising antimicrobial resins on substrate surfaces are disclosed. The methods involve providing a mixture comprising about 15 weight % to about 80 weight % of a hydrophilic acrylic oligomer, about 10 weight % to about 80 weight % of a multifunctional acrylic monomer, about 5 weight % to about 40 weight % of an adhesion-promoting acrylic or vinyl monomer, and about 0.1 weight % to about 15 weight % of a metal salt; and exposing the mixture to a radiation source to cure at least a portion of the mixture, thereby forming an antimicrobial resin.

31 Claims, 2 Drawing Sheets

U.S. PATENT DOCUMENTS

| | | |
|---|---|---|
| 6,605,751 B1 | 8/2003 | Gibbins et al. |
| 6,645,444 B2 | 11/2003 | Goldstein |
| 6,669,681 B2 | 12/2003 | Jepson et al. |
| 6,682,509 B2 | 1/2004 | Lopez |
| 6,706,201 B1 | 3/2004 | Meyer et al. |
| 6,716,891 B1 | 4/2004 | Meisenburg et al. |
| 6,716,895 B1 | 4/2004 | Terry |
| 6,780,332 B2 | 8/2004 | Shiau et al. |
| 6,783,690 B2 | 8/2004 | Kologe et al. |
| 6,800,278 B1 | 10/2004 | Perrault et al. |
| 6,849,214 B2 | 2/2005 | Patil |
| 6,852,771 B2 | 2/2005 | Balch et al. |
| 6,878,757 B2 | 4/2005 | Roby |
| 6,897,349 B2 | 5/2005 | Gibbins et al. |
| 6,908,681 B2 | 6/2005 | Terry et al. |
| 6,921,390 B2 | 7/2005 | Bucay-Couto et al. |
| 6,949,598 B2 | 9/2005 | Terry |
| 6,984,392 B2 | 1/2006 | Bechert et al. |
| 7,179,849 B2 | 2/2007 | Terry |
| 7,232,777 B1 | 6/2007 | Van Hyning |
| 7,288,264 B1 | 10/2007 | Sawan et al. |
| 7,345,980 B2 | 3/2008 | Richard |
| 7,378,156 B2 | 5/2008 | Terry |
| 2001/0023250 A1* | 9/2001 | Spada et al. ............ 514/250 |
| 2003/0031872 A1 | 2/2003 | Arps et al. |
| 2003/0129322 A1 | 7/2003 | Kunz et al. |
| 2003/0141477 A1 | 7/2003 | Miller |
| 2003/0157147 A1 | 8/2003 | Hoge et al. |
| 2003/0157176 A1 | 8/2003 | Nakamura et al. |
| 2003/0165633 A1 | 9/2003 | Ryu et al. |
| 2003/0198821 A1 | 10/2003 | Terry et al. |
| 2003/0208165 A1 | 11/2003 | Christensen et al. |
| 2004/0052831 A1 | 3/2004 | Modak et al. |
| 2004/0106341 A1 | 6/2004 | Vogt et al. |
| 2004/0229034 A1 | 11/2004 | Djokic |
| 2005/0003019 A1 | 1/2005 | Petersen |
| 2005/0008676 A1 | 1/2005 | Qiu et al. |
| 2005/0013842 A1 | 1/2005 | Qiu et al. |
| 2005/0019533 A1* | 1/2005 | Mossbrook et al. ........ 428/204 |
| 2005/0064176 A1 | 3/2005 | Terry |
| 2005/0147919 A1 | 7/2005 | Kunz et al. |
| 2005/0147979 A1 | 7/2005 | Koo et al. |
| 2005/0226931 A1* | 10/2005 | Gibbins et al. ............ 424/486 |
| 2006/0068024 A1 | 3/2006 | Schroeder et al. |
| 2006/0085036 A1 | 4/2006 | Viola |
| 2006/0090596 A1 | 5/2006 | Goia et al. |
| 2006/0140994 A1 | 6/2006 | Bagwell et al. |
| 2006/0141015 A1 | 6/2006 | Tessier et al. |
| 2006/0167180 A1 | 7/2006 | Plaut et al. |
| 2006/0216327 A1 | 9/2006 | Madsen et al. |
| 2006/0222971 A1 | 10/2006 | Seo et al. |
| 2006/0257681 A1 | 11/2006 | Wolf et al. |
| 2006/0269485 A1 | 11/2006 | Friedman et al. |
| 2007/0003603 A1 | 1/2007 | Karandikar et al. |
| 2007/0048356 A1 | 3/2007 | Schorr et al. |
| 2007/0050007 A1 | 3/2007 | Kondyurin et al. |
| 2007/0085036 A1 | 4/2007 | Santhouse |
| 2007/0098806 A1 | 5/2007 | Ismail et al. |
| 2007/0154506 A1 | 7/2007 | Patton et al. |
| 2007/0207335 A1 | 9/2007 | Karandikar et al. |
| 2007/0212381 A1 | 9/2007 | DiFiore et al. |
| 2007/0254044 A1 | 11/2007 | Karandikar et al. |
| 2008/0021381 A1 | 1/2008 | Lurvey et al. |
| 2008/0021392 A1 | 1/2008 | Lurvey et al. |
| 2008/0027410 A1 | 1/2008 | Harding et al. |
| 2008/0063693 A1 | 3/2008 | Cook et al. |
| 2008/0181931 A1 | 7/2008 | Qiu et al. |
| 2009/0314628 A1 | 12/2009 | Lee et al. |
| 2009/0317435 A1 | 12/2009 | Vandesteeg et al. |
| 2009/0324738 A1 | 12/2009 | Krongauz |

FOREIGN PATENT DOCUMENTS

| | | |
|---|---|---|
| EP | 0190504 | 8/1986 |
| EP | 0328421 | 8/1989 |
| GB | 2000788 | 1/1979 |
| JP | 56/082504 A | 7/1981 |
| JP | 8133919 A | 5/1996 |
| JP | 2007182605 | 7/2007 |
| WO | WO-94/22522 | 10/1994 |
| WO | WO-01/43788 | 6/2001 |
| WO | WO-02/083156 | 10/2002 |
| WO | WO-2006/026026 | 3/2006 |
| WO | WO-2006/006706 | 6/2006 |
| WO | WO2006/056482 A1 * | 6/2006 |
| WO | WO-2006/074117 A2 | 7/2006 |
| WO | WO-2006/099906 | 9/2006 |
| WO | WO-2007/000590 | 1/2007 |
| WO | WO-2007/028607 | 3/2007 |
| WO | WO-2007/070649 | 6/2007 |
| WO | WO-2007095058 A2 | 8/2007 |
| WO | WO-2007/104107 | 9/2007 |
| WO | WO-2008/031601 | 3/2008 |
| WO | WO-2008/036377 | 3/2008 |
| WO | WO-2008/068154 | 6/2008 |
| WO | WO-2008/145750 | 12/2008 |
| WO | WO-2009154905 A1 | 12/2009 |

OTHER PUBLICATIONS

Humar et al., Prospective randomized trial 10% povidone-iodine versus 0.5% tincture of chlorhexidine as cutaneous antisepsis for prevention of central venous catheter infection, *Clinical Infectious Diseases*, 31:1001-7 (2000).

O'Grady et al., *Guidelines for the Prevention of Intravascular Catheter-Related Infections*, MMWR Recommendations and Reports, 51(RR10):1-26 (Aug. 9, 2002).

Office action (nonfinal) from U.S. Appl. No. 12/164,414, dated Apr. 30, 2010.

Office action (nonfinal) from U.S. Appl. No. 12/143,304, dated May 26, 2010.

Belfield et al., *Photoinitiated Polymerization*, ACS Symposium Series 847, American Cancer Society, Washington DC (2003).

Brown (ed.), *Chemistry: The Central Science*, 6th edition, Prentice Hall (2002).

Dean, Table 8.6, In: *Lange's Handbook of Chemistry*, 15th ed., McGraw Hill (1998).

Fan et al., "Chemical, electrochemical, gravimetric, and microscopic studies on antimicrobial silver films", *J. Phys. Chem. B*, 106:279-87 (2002).

Jacobs et al., "Thermodynamics of complex formation reactions in non-aqueous solvents : Part 2. Reaction of silver(I) with $N,N,N',N'$-tetramethylene diamine in acetone, methanol and ethanol", *Thermochimica Acta*, 127:399-402 (1988).

Kampf et al., "Microbicidal activity of a new silver-containing polymer, SPI-ARGENT II", *Antimicrob Agents Chemother.*, 42:2440-2 (1998).

Kapoor, "Preparation, characterization, and surface modification of silver particles," *Langmuir*, 14:1021-5 (1998).

Kashiwagi et al., "Facile size-regulated synthesis of silver nanoparticles by controlled thermolysis of silver alkylcarboxylates in the presence of alkylamines with different chain lengths", *J. Colloid Interface Sci.*, 300:169-75 (2006).

Klang, *Radiation Curable Hyperbranched Polyester Acrylates*, Sartomer Company, Exton, Pennsylvania (Mar. 2008) (6 pp.).

Klasen, "A historical review of the use of silver in the treatment of burns. II. Renewed interest for silver", *Burns*, 26:131-8 (2000).

Krongauz et al., *Processes in Photoreactive Polymers*, New York, NY: Chappman & Hall (1995).

Russell et al., "Antimicrobial activity and action of silver", *Prog. Med. Chem.*, 31:351-70 (1994).

Sartomer Co. Product Bulletin, *Hydrophilic vs. Hydrophobic Monomers* (Exton, Penn.) Dec. 2004 (8 pp.).

*Solubility Product Constants*, from University of Split Faculty of Chemistry and Technology website <URL:http://www.ktf-split.hr> downloaded Jun. 16, 2008 (6 pp.).

Van Poucke, "The thermodynamics of ethylene-diamine complexes of silver," *Talanta*, 23:161-2 (1976).

Yamamoto et al., "Size-controlled synthesis of monodispersed silver nanoparticles capped by long-chain alkyl carboxylates from silver carboxylate and tertiary amine," *Langmuir*, 22:8581-6 (2006).

Zwanenburg, *How to Formulate UV-Curing Coatings*, (Verneuil en Hallatte, France) (2008) (20 pp.).

International Search Report and Written Opinion from corresponding International Application No. PCT/US2009/043942, dated Oct. 26, 2009 (10 pp.).

Bacterin International Inc., *Bacterin: The Smart Coating*, Slide Presentation (8 pages), Available Apr. 8, 2008.

Bailey et al., "The electrochemistry and kinetics of the silver-triiodide reaction," *Electrochimica Acta*, 22:35-40 (1977).

Broome et al. "Complex formation with high molecular weight amines. I." *J. Am. Chem. Soc.*, 68:67-69 (1946).

Campbell et al., "The chemical iodination of silver," *Australian J. Chem.*, 39:827-837 (1986).

Clement et al., "Antibacterial silver," *Metal Based Drugs*, 1:467-482 (1994).

Dai et al., "2D and 3D silver(I) ethylenediamine coordination polymers with Ag-Ag argentophilic interaction," *Z. Naturforsch*, 62b: 1112-1116 (2007).

Dong et al., Silver carboxylate nanostructure nucleation and growth on AgBr crystals, *Nanotechnology*, 16:S592-S600 (2005).

Duff et al., "The microstructure of colloidal silver: evidence for a polytetrahedral growth sequence," *J. Chem. Soc., Chem. Comm.*, 16:1264-1266 (1987).

Hozumi et al., "Spatially defined silver mirror reaction on micropatterned aldehyde-terminated self-assembled monolayer," *Appl. Surface Science*, 252:6111-6114 (2006).

Kang et al., Surface chemistry of ethylenediamine ($NH_2$-$CH_2CH_2NH_2$) on Pt(111), *Surface Science*, 470: L13-L19 (2000).

Lansdown, "Silver in health care: antimicrobial effects and safety in use," In: Hipler et al. (eds.), Biofunctional Textiles and the Skin. *Curr. Probl. Dermatol*. Basel: Karger, 33:17-34 (2006).

Magyar et al., "The silver(I) complexes of ethylenediamine in solution," *Acta Chem. Scand. A*, 32:943-955 (1978).

Mills et al., "Formation of $\mu_2$,$\eta^2$-Diaminoethylene ($H_2NCCNH_2$) from Cyanogen ($C_2N_2$) and Hydrogen on Pt(111): Characterization of a Diiminium Surface Species," *J.Am. Chem. Soc.*, 118:6524-6525 (1996).

Newman et al., "The infrared spectra and structures of some silver-ethylenediamine complexes," *J. Chem. Soc.*, 3447-3450 (1962).

Nielsen et al., "The basis for colored silver-protein complex formation in stained polyacrylamide gels," *Anal. Biochem.*, 141:311-315 (1984).

Olson et al., "The simple yet elusive crystal structure of silver acetate and the role of the Ag-Ag bond in the formation of silver nanoparticles during the thermally induced reduction of silver carboxylates" *Chem. Mater.*, 18:1667-1674 (2006).

Patra et al., "The synthesis and characterization of a series of bis-bidentate Schiff base ligands and their coordination complexes with silver(I), copper(I) and zinc(II) d10 metal ions," *New J. Chem.*, 27:1124-1131 (2003).

Qu et al., "Novel silver nanostructures from silver mirror reaction on reactive substrates," *J. Phys. Chem. B*, 109:13985-13990 2005.

Qu et al., "Synthesis and crystal structure of copper II and silver I complex with 1,4-diazabicyclo[2.2.2]octane[$Cu(CBC)_2(Dabco)(H_2O)]_n$ (1) and $[Ag_2(HBC)_2(Dabco)]_n$ (2) "*J. Chem. Crystallogr*. 37: 579-582 (2007).

Rabii et al., "Measurement and control of thin film uniformity in hollow glass waveguides," *Opt. Eng.*, 38:2009-2015 (1999).

Richards et al., Chapter I: Synthetic approaches to metallic nanomaterials, In: Kumar et al. (eds.), *Nanofabrication Towards Biomedical Applications: Techniques, Tools, Applications, and Impact*, 1st edition, Wiley-VCH, pp. 3-32 (2005).

Ross et al., *Colloidal Systems and Interfaces*, J. Wiley & Sons (1988).

Satoshi et al., "Bleach-fixer using a new biodegradable chelating agent," *Konika Technical Report*, 16:13-18 (2003).

Southeast Missouri State University, *CH186 Lecture Presentation: Transition Metal/Coordination Chemistry*. Retrieved from the Internet, Nov. 3, 2008: <URL: http://chemistry.semo.edu/crawford/ch186/lectures/ch20/>.

Starovoytov et al., "Dissolution behavior of silver in ammoniacal solutions using bromine, iodine and hydrogen-peroxide as oxidants," *Hydrometallurgy*, 86:114-119 (2007).

Tammann et al., "Uber anlauffarben von metallen," *Allg. Chem.*, 111:78-89 (1920). [German Only].

University of Waterloo, *Coordination Chemistry*. Retrieved from the Internet. Nov. 10, 2008: <URL: http://www.science.uwaterloo.ca/~cchieh/cact/cact.html>.

University of Waterloo, *Cyberspace Chemistry (CaCt)*. Retrieved from the Internet, Nov. 3, 2008: <URL: http://www.science.uwaterloo.ca/~cchieh/cact/cact.html >.

Yilmaz et al., "Silver(I) saccharinato complexes with ethylenediamine and N,N-Dimethylethylenediamine—$[Ag_2(sac)_2(en)(H_2O)]_n$ and $[Ag_2 (sac)_2 (dmen)_2]$," *Z. Anorg. Ally. Chem.*, 631:1961-1965 (2005).

Zhai et al., "Silver colloids and interfacial colloids-adsorption of alizarin yellow 2G and its effect on colloidal nulcleation," *Langmuir*, 13:420-425 (1997).

Partial English Translation of Japanese Patent No. JP8133919A (6 pages).

Partial English Translation of Japanese Patent No. JP56-82504A (2 pages).

Final office action, U.S. Appl. No. 12/143,319, dated Feb. 17, 2012.

Nonfinal office action, U.S. Appl. No. 12/400,439, dated Dec. 23, 2011.

* cited by examiner

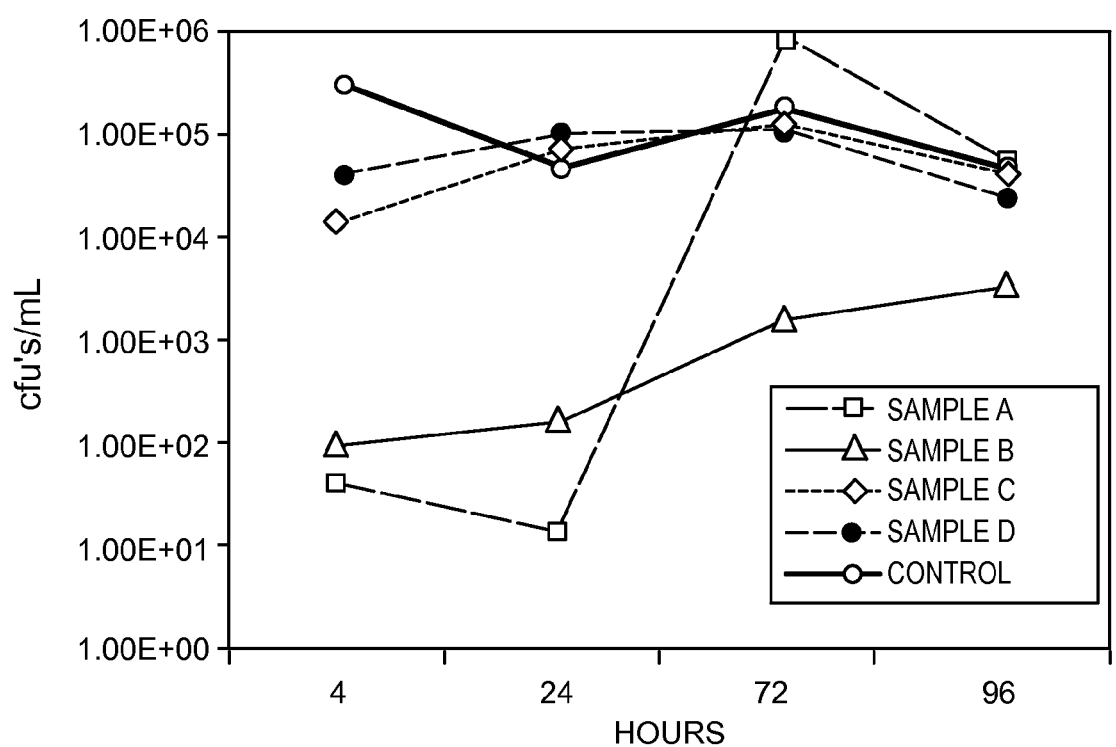

METHODS FOR MAKING ANTIMICROBIAL RESINS

BACKGROUND

1. Field of the Disclosure

The disclosure relates generally to antimicrobial resin compositions and methods for making such resins. More particularly, the disclosure is directed to methods of making antimicrobial resin compositions comprising antimicrobial metal salts and methods for forming such resins on substrates, such as medical devices.

2. Brief Description of Related Technology

Even brief exposure to surfaces contaminated with microbes can introduce bacterial, viral, fungal, or other undesirable infections to humans and other animals. Of particular concern is preventing or reducing microbial infection associated with the use of invasive medical devices such as catheters, intravenous fluid administration systems, and similar medical devices which require prolonged patient contact and thus present significant infection risks. Contamination may result from the patients' own flora or from one or more healthcare workers' hands during insertion and/or manipulation of the device, or from both the patient and healthcare worker. Medical devices coated with antimicrobial materials can reduce the transfer of such microbes to patients, thereby improving the safety and efficacy of these devices. Such antimicrobial coatings often include silver metal or silver salts, or other metals with demonstrable antimicrobial activity such as copper, gold, zinc, cerium, platinum, palladium, or tin.

Silver and salts thereof are commonly used in antimicrobial coatings because of their demonstrated broad spectrum antimicrobial activity against various bacteria, viruses, yeast, fungi, and protozoa. It is theorized that the observed antimicrobial activity is primarily due to the ability of silver ions to tightly bind nucleophilic functional groups containing sulfur, oxygen or nitrogen. Many nucleophilic functional groups such as thiols, carboxylates, phosphates, alcohols, amines, imidazoles, and indoles are prevalent in biomolecules. Upon binding of ionized silver to these various nucleophilic functional groups, it is believed that widespread disruption and inactivation of microbial biomolecules (and thus antimicrobial activity) occurs.

Silver and salts thereof have therefore been used as antimicrobial agents in a wide variety of applications; for example, they have been incorporated in the absorbent materials of wound care products such as dressings, gels, and bandages, and also in compositions for providing antimicrobial coatings on medical devices. Polymeric components frequently are added to such silver- or silver salt-containing compositions in order to facilitate manufacturing and/or deposition. One disadvantage of such antimicrobial compositions, however, is their characteristic poor adhesion to substrate surfaces. Strong adhesion to surfaces is frequently desirable to maintain continued release of the antimicrobial agent over a period of time and to avoid loss of the antimicrobial coating by routine contact with a patient or healthcare worker. Many polymer-containing metal or metal salt compositions also exhibit unsatisfactory antimicrobial efficacy profiles. Various factors can contribute to undesirable efficacy profiles, such as poorly dispersed or settled particles of the metal or metal salt, deformation of the coating during curing, or decomposition of the metal or metal salt during subsequent sterilization treatments. Poor dispersion of the metal or metal salt in the composition, for example, can result in heterogeneous release of the metal or metal salt, while a well-dispersed metal or metal salt generally elutes from the composition according to more homogeneous spatial and/or temporal release profiles. Another disadvantage of many polymer-containing metal or metal salt compositions is the heterogeneous crosslinked structure that can result, for example, from long polymer cure times and/or imprecise control of the polymer curing conditions. Long polymer cure times and/or imprecisely controlled polymer curing conditions, for example, can disadvantageously contribute to the formation of poorly dispersed or settled metals or metal salts, and thus can produce compositions having heterogeneous elution profiles.

A disadvantage of antimicrobial compositions comprising metals instead of metal salts is their characteristic color/opaqueness, which prevents a healthcare provider from being able to see through the medical device substrate. Silver coatings, for example, are generally brown in color. Thus, when silver coatings are applied to transparent surfaces, the coated surfaces typically have a brown color and significantly diminished transparency. In contrast to coatings comprising metallic silver, many coatings comprising silver salts are transparent or translucent, and/or lack a colored appearance. Thus, when silver salt coatings are applied to transparent surfaces, the coated surfaces typically have little color and are highly transparent.

SUMMARY

The present disclosure is directed to methods for forming antimicrobial resins. The methods include providing a mixture comprising a hydrophilic acrylic oligomer, a multifunctional acrylic monomer, an adhesion-promoting acrylic or vinyl monomer, and an antimicrobial metal salt; and exposing the mixture to a radiation source to cure at least a portion of the mixture, thereby forming an antimicrobial resin. The methods further include forming medical devices or medical components comprising the antimicrobial resin. In accordance with the present methods, the antimicrobial resin can be applied to a substrate surface to form a coating on the substrate surface. Alternatively, a coating comprising an antimicrobial resin can be formed by providing the mixture on a substrate surface before exposing the mixture to the radiation source.

The substrate surfaces can comprise plastics, glasses, metals, ceramics, elastomers, or mixtures or laminates thereof. The substrate surfaces can comprise surfaces of medical devices or medical device components. Preferred examples of substrate surfaces include polycarbonate medical devices. The substrate surface also can comprise surfaces of medical fluid containers or medical fluid flow systems. Preferred examples of medical fluid flow systems include I.V. sets and components thereof, such as, for example, luer access devices.

The antimicrobial metal salt can comprise various metals or mixtures of metals. Preferred metal salts include salts of silver, copper, gold, zinc, cerium, platinum, palladium, and tin.

The radiation source can be an ultraviolet (UV) light source, an electron beam source, a gamma radiation source, an X-ray source, an ion beam source, a microwave source, a heat source, or other radiation sources.

The hydrophilic acrylic oligomer includes acrylic oligomers and mixtures of acrylic oligomers having one or more acrylate, methacrylate, acrylamide, or methacrylamide functional groups. The hydrophilic acrylic oligomer also includes acrylic oligomers having combinations of the foregoing functional groups.

The multifunctional acrylic monomer includes acrylate esters, methacrylate esters, acrylamides, methacrylamides, and mixtures of the foregoing having more than one acrylate, methacrylate, acrylamide, or methacrylamide functional groups. The multifunctional acrylic monomer also includes acrylic monomers having combinations of the foregoing functional groups.

The adhesion-promoting acrylic or vinyl monomer includes acrylate esters, methacrylate esters, acrylamides, methacrylamides, and mixtures of the foregoing having one or more acrylate, methacrylate, acrylamide, or methacrylamide functional groups. The adhesion-promoting acrylic or vinyl monomer also includes acrylic monomers having combinations of the foregoing functional groups and monomers having vinyl groups.

BRIEF DESCRIPTION OF THE DRAWINGS

FIG. 3 is a graph showing the growth over time in colony forming units (cfu) per mL of S. aureus on a polycarbonate substrate surface carrying a coating comprising a cured antimicrobial resin prepared in accordance with the methods of the disclosure (Sample B), compared to (i) substrate surfaces carrying coatings comprising antimicrobial resins not prepared in accordance with the methods of the disclosure (Sample A, Sample C, and Sample D) and (ii) an uncoated control substrate surface.

DETAILED DESCRIPTION

Figure 1:
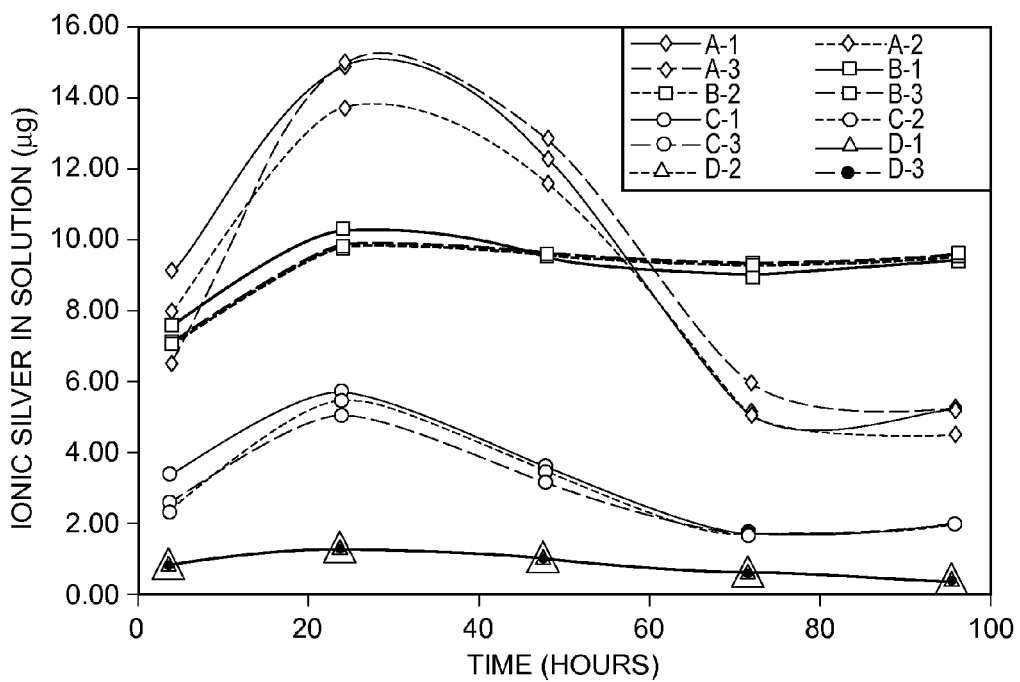
FIG. 1 is a graph showing the release of silver ions over time from substrate surfaces carrying an antimicrobial resin prepared in accordance with the methods of the disclosure (B-1, B-2, B-3), compared to substrate surfaces carrying antimicrobial resins not prepared in accordance with the methods of the disclosure (A-1, A-2, A-3, C-1, C-2, C-3, D-1, D-2, D-3).

The present disclosure is directed to methods for forming antimicrobial resins. The methods involve providing a mixture comprising about 15 weight % to about 80 weight % of a hydrophilic acrylic oligomer, about 10 weight % to about 80 weight % of a multifunctional acrylic monomer, about 5 weight % to about 40 weight % of an adhesion-promoting acrylic or vinyl monomer, and about 0.1 weight % to about 15 weight % of an antimicrobial metal salt; and exposing the mixture to a radiation source to cure at least a portion of the mixture, thereby forming an antimicrobial resin. The methods further include forming medical devices or medical components comprising the antimicrobial resin. In accordance with the present methods, the antimicrobial resin can be applied to a substrate surface to form a coating on the substrate surface. In some embodiments, the multifunctional acrylic monomer and the adhesion promoting acrylic or vinyl monomer can be the same compound.

The present disclosure also is directed to methods for forming a coating comprising an antimicrobial resin. The methods involve providing a mixture comprising about 15 weight % to about 80 weight % of a hydrophilic acrylic oligomer, about 10 weight % to about 80 weight % of a multifunctional acrylic monomer, about 5 weight % to about 40 weight % of an adhesion-promoting acrylic or vinyl monomer, and about 0.1 weight % to about 15 weight % of an antimicrobial metal salt; providing the mixture on a substrate surface before exposing the mixture to a radiation source; and exposing the mixture to the radiation source to cure at least a portion of the mixture, thereby forming a coating comprising an antimicrobial resin.

As previously discussed, many polymer-containing metal or metal salt compositions adhere poorly to substrate surfaces and/or exhibit unsatisfactory antimicrobial efficacy profiles. Forming antimicrobial resins according to the methods disclosed herein can advantageously improve the dispersion of the metal salt in the resin composition, prevent settling of the metal salt during the curing process, prevent deformation (e.g., shrinking) of the resin during the curing process, and/or produce more homogeneously crosslinked resins. Accordingly, antimicrobial resins prepared according the methods disclosed herein can display improved efficacy profiles. Furthermore, coatings comprising the antimicrobial resin can display increased adhesion to substrate surfaces. Accordingly, the disclosed methods can provide efficient methods for obtaining medical devices comprising a strongly adherent and/or more efficacious antimicrobial coating and, in general, more efficacious antimicrobial resins.

As described above, many metal-containing compositions are disadvantageously opaque or colored. Irradiation of compositions containing metal salts can reduce the metal salts, thereby producing compositions comprising metals that can give the composition an opaque or colored appearance. Surprisingly, and contrary to the expectations of one of ordinary skill in the art, antimicrobial resins and coatings thereof prepared by radiation curing in accordance with the present disclosure can advantageously be substantially transparent/translucent (upon visual inspection), i.e., generally lacking a colored appearance, despite including ionic metal that one of ordinary skill would expect to be reduced by the radiation used in the curing process, thereby forming the corresponding metal which generally causes the compositions to become colored. Additionally, radiation curing of the antimicrobial resins of the present disclosure can beneficially obviate the need for downstream sterilization processing because the resin can be sterilized by radiation during the curing process.

The substrate surfaces of the present disclosure can comprise various materials including, for example, glasses, metals, plastics, ceramics, and elastomers, as well as mixtures and/or laminates thereof. Suitable examples of plastics include, but are not limited to, acrylonitrile butadiene styrenes, polyacrylonitriles, polyamides, polycarbonates, polyesters, polyetheretherketones, polyetherimides, polyethylenes such as high density polyethylenes and low density polyethylenes, polyethylene terephthalates, polylactic acids, polymethyl methyacrylates, polypropylenes, polystyrenes, polyurethanes, poly(vinyl chlorides), polyvinylidene chlorides, polyethers, polysulfones, silicones, and blends and copolymers thereof. Suitable elastomers include, but are not limited to, natural rubbers, and synthetic rubbers, such as styrene butadiene rubbers, ethylene propylene diene monomer rubbers (EPDM), polychloroprene rubbers (CR), acrylonitrile butadiene rubbers (NBR), chlorosuphonated polyethylene rubbers (CSM), polyisoprene rubbers, isobutylene-isoprene copolymeric rubbers, chlorinated isobutylene-isoprene copolymeric rubbers, brominated isobutylene-isoprene copolymeric rubbers, and blends and copolymers thereof.

In one preferred embodiment of the present disclosure, the antimicrobial resin is formed on (or applied to) a surface of a medical device or medical device component. Medical devices and medical device components which can benefit from the methods according to the disclosure, include, but are not limited to, instruments, apparatuses, implements, machines, contrivances, implants, and components and accessories thereof, intended for use in the diagnosis, cure, mitigation, treatment, or prevention of disease or other condition in humans or other animals, or intended to affect the structure or any function of the body of humans or other animals. Such medical devices are described, for example, in the official National Formulary, the United States Pharmacopoeia, and any supplements thereto. Representative medical devices include, but are not limited to: catheters, such as venous catheters, urinary catheters, Foley catheters, and pain management catheters; dialysis sets; dialysis connectors; stents; abdominal plugs; feeding tubes; indwelling devices; cotton gauzes; wound dressings; contact lenses; lens cases; bandages; sutures; hernia meshes; mesh-based wound coverings; surgical tools; medical monitoring equipment including, but not limited to the touch screen displays often used in conjunction with such equipment; medical pumps; pump housings; gaskets such as silicone O-rings; needles; syringes; surgical sutures; filtration devices; drug reconstitution devices; implants, metal screws, and metal plates. Additional exemplary medical devices include, but are not limited to, medical fluid containers, medical fluid flow systems, infusion pumps, and medical devices such as stethoscopes which regularly come into contact with a patient. One example of a medical fluid flow system is an intravenous fluid administration set, also known as an I.V. set, used for the intravenous administration of fluids to a patient. A typical I.V. set uses plastic tubing to connect a phlebotomized subject to one or more medical fluid sources, such as intravenous solutions or medicament containers. I.V. sets optionally include one or more access devices providing access to the fluid flow path to allow fluid to be added to or withdrawn from the IV tubing. Access devices advantageously eliminate the need to repeatedly phlebotomize the subject and allow for immediate administration of medication or other fluids to the subject, as is well known. Access devices can be designed for use with connecting apparatus employing standard luers, and such devices are commonly referred to as "luer access devices," "luer-activated devices," or "LADs." LADs can be modified with one or more features such as antiseptic indicating devices. Various LADs are illustrated in U.S. Pat. Nos. 5,242,432, 5,360,413, 5,730,418, 5,782,816, 6,039,302, 6,669,681, and 6,682,509, and U.S. Patent Application Publication Nos. 2003/0141477, 2003/0208165, 2008/0021381, and 2008/0021392, the disclosures of which are hereby incorporated by reference in their entireties.

I.V. sets can incorporate additional optional components including, for example, septa, stoppers, stopcocks, connectors, protective connector caps, connector closures, adaptors, clamps, extension sets, filters, and the like. Thus, suitable medical devices and medical device components which may be processed in accordance with the methods of the present disclosure include, but are not limited to: I.V. tubing, I.V. fluid bags, I.V. set access devices, septa, stopcocks, I.V. set connectors, I.V. set connector caps, I.V. set connector closures, I.V. set adaptors, clamps, I.V. filters, catheters, needles, stethoscopes, and cannulae. Representative access devices include, but are not limited to: luer access devices including, but not limited to, needleless luer access devices.

The surface of the medical device or medical device component can be fully or partially coated with the antimicrobial resin. The coating can be formed on (or applied to) an exterior surface of the device (i.e., a surface which is intended to come into contact with a patient or healthcare provider), an interior surface of the device (i.e. a surface which is not intended to come into contact with a patient or healthcare provider, but which can come into contact with the patient's blood or other fluids), or both. Suitable medical devices and medical device components are illustrated in U.S. Pat. Nos. 4,412,834, 4,417,890, 4,440,207, 4,457,749, 4,485,064, 4,592,920, 4,603,152, 4,738,668, 5,630,804, 5,928,174, 5,948,385, 6,355,858, 6,592,814, 6,605,751, 6,780,332, 6,800,278, 6,849,214, 6,878,757, 6,897,349, 6,921,390, and 6,984,392, and U.S. Patent Application Publication No. 2007/0085036, the disclosures of which are hereby incorporated by reference in their entireties.

The resins of the present disclosure comprise metal salts having antimicrobial properties. Suitable metal salts for use in the resins include, but are not limited to, salts of silver, copper, gold, zinc, cerium, platinum, palladium, and tin. Antimicrobial resins comprising a combination of two or more of the foregoing metals can also be used.

Hydrophilic Acrylic Oligomers

Antimicrobial resin compositions in accordance with the present disclosure are prepared from a mixture comprising about 15 weight % to about 80 weight % of a hydrophilic acrylic oligomer. Suitable ranges include, but are not limited to, about 25 weight % to about 60 weight %, and/or about 35 weight % to about 50 weight %. The mixture can comprise, for example, about 15 weight % to about 25 weight %, about 25 weight % to about 35 weight %, about 35 weight % to about 45 weight %, about 45 weight % to about 55 weight %, about 55 weight % to about 65 weight %, and/or about 65 weight % to about 80 weight % of the acrylic oligomer. Mixtures including more than one acrylic oligomer also can be used.

In accordance with the present disclosure, the hydrophilic acrylic oligomer can comprise acrylate oligomers, methacrylate oligomers, acrylamide oligomers, methacrylamide oligomers, or mixtures of the foregoing. The acrylic oligomers can be monofunctional oligomers (i.e., oligomers having one acrylate, methacrylate, acrylamide, or methacrylamide group). The acrylic oligomers also can be difunctional oligomers (i.e., oligomers having two acrylate, methacrylate, acrylamide, or methacrylamide groups), trifunctional oligomers (i.e., oligomers having three acrylate, methacrylate, acrylamide, or methacrylamide groups), tetrafunctional oligomers (i.e., oligomers having four acrylate, methacrylate, acrylamide, or methacrylamide groups), pentafunctional oligomers (i.e., oligomers having five acrylate, methacrylate, acrylamide, or methacrylamide groups), or hexafunctional oligomers (i.e., oligomers having six acrylate, methacrylate, acrylamide, or methacrylamide groups). Acrylic oligomers having more than one functional group can comprise the same functional groups or different functional groups. A trifunctional acrylic oligomer, for example, can comprise two acrylate groups and one acrylamide group. A trifunctional acrylic oligomer also can comprise, for example, three acrylate groups. Acrylic oligomers having more than six functional groups (e.g., eight or ten functional groups) and mixtures of the foregoing acrylic oligomers also can be used.

Suitable hydrophilic acrylic oligomers include, but are not limited to: polyepoxy acrylates, polyurethane acrylates, polyester acrylates, polyether acrylates, amine-modified polyether acrylates, polyacrylic acrylates, polycarbonate acrylates, polyepoxy methacrylates, polyurethane methacrylates, polyester methacrylates, polyether methacrylates, amine-modified polyether methacrylates, polyacrylic methacrylates, polycarbonate methacrylates, polyepoxy acrylamides, polyurethane acrylamides, polyester acrylamides, polyether acrylamides, amine-modified polyether acrylamides, polyacrylic acrylamides, polycarbonate acrylamides, polyepoxy methacrylamides, polyurethane methacrylamides, polyester methacrylamides, polyether methacrylamides, amine-modified polyether methacrylamides, polyacrylic methacrylamides, polycarbonate methacrylamides, and mixtures of the foregoing. As discussed above, the foregoing acrylic oligomers include one or more functional groups, for example, one to six functional groups.

Suitable polyepoxy acrylate oligomers include, but are not limited to: aromatic difunctional epoxy acrylates, acrylated oil epoxy acrylates, phenol formaldehyde epoxy acrylates (also known as novolac epoxy acrylates), aliphatic epoxy acrylates, and mixtures of the foregoing.

Exemplary hydrophilic acrylic oligomers include, but are not limited to: ethoxylated bisphenol A diacrylates (e.g., 30 mole ethoxylated bisphenol A diacrylate), ethoxylated bisphenol A dimethacrylates (e.g., 10 mole ethoxylated bisphenol A dimethacrylate), polyethylene glycol diacrylates, polyethylene glycol dimethacrylates, methoxy polyethylene glycol acrylates, methoxy polyethylene glycol methacrylates, polypropylene glycol diacrylates, polypropylene glycol dimethacrylates, methoxy polypropylene glycol acrylates, methoxy polypropylene glycol methacrylates, and mixtures of the foregoing. Ethoxylated acrylates and methacrylates typically include about 4 to about 100 ethoxy groups, for example, about 6 to about 70, about 8 to about 50, about 10 to about 40, and/or about 12 to about 30 ethoxy groups. Oligomers containing polyethylene glycol or polypropylene glycol typically have molecular weights of about 100 g/mol to about 2000 g/mol, for example, about 150 g/mol to about 1000 g/mol, about 200 g/mol to about 800 g/mol, and/or about 300 g/mol to about 600 g/mol.

Multifunctional Acrylic Monomers

Antimicrobial resin compositions in accordance with the present disclosure are prepared from a mixture comprising about 10 weight % to about 80 weight % of a multifunctional acrylic monomer. Suitable ranges include, but are not limited to, about 20 weight % to about 60 weight %, and/or about 30 weight % to about 50 weight %. The mixture can comprise, for example, about 10 weight % to about 20 weight %, about 20 weight % to about 30 weight %, about 30 weight % to about 40 weight %, about 40 weight % to about 50 weight %, about 50 weight % to about 60 weight %, about 60 weight % to about 70 weight %, and/or about 70 weight % to about 80 weight % of the multifunctional acrylic monomer. Mixtures including more than one acrylic monomer also can be used.

In accordance with the present disclosure, the multifunctional acrylic monomer can comprise acrylate esters, methacrylate esters, acrylamides, methacrylamides, or mixtures of the foregoing. The multifunctional acrylic monomers can be difunctional monomers (i.e., monomers having two acrylate, methacrylate, acrylamide, and/or methacrylamide groups). The multifunctional acrylic monomers also can be trifunctional monomers, tetrafunctional monomers, pentafunctional monomers, hexafunctional monomers, or mixtures of the foregoing. Multifunctional acrylic monomers can comprise the same functional groups or different functional groups. A difunctional acrylic monomer, for example, can comprise one acrylate group and one methacrylamide group. A difunctional acrylic monomer also can comprise, for example, two methacrylate groups. Multifunctional acrylic monomers having more than six functional groups (e.g., eight or ten functional groups) and mixtures of the foregoing acrylic monomers also can be used. When exposed to suitable conditions (e.g., a radiation source, optionally in the presence of an initiator), the alkenyl functional groups of the multifunctional acrylic monomers can undergo intermolecular reactions to form, for example, crosslinked structures.

Suitable multifunctional acrylic monomers include, but are not limited to: alkoxylated acrylates; alkoxylated methacrylates; linear, branched, or cyclic alkyl acrylates; linear, branched, or cyclic alkyl methacrylates; linear, branched, or cyclic alkyl acrylamides; linear, branched, or cyclic alkyl methacrylamides; linear, branched, or cyclic alkenyl acrylates; linear, branched, or cyclic alkenyl methacrylates; linear, branched, or cyclic alkenyl acrylamides; linear, branched, or cyclic alkenyl methacrylamides; alkoxylated linear, branched, or cyclic alkyl acrylates; alkoxylated linear, branched, or cyclic alkyl methacrylates; alkoxylated linear, branched, or cyclic alkenyl acrylates; alkoxylated linear, branched, or cyclic alkenyl methacrylates; heterocyclic acrylates; heterocyclic methacrylates; heterocyclic acrylamides; heterocyclic methacrylamides; and mixtures of the foregoing. Difunctional, trifunctional, tetrafunctional, pentafunctional, and hexafunctional derivatives of the foregoing are included.

Alkoxylated multifunctional acrylate monomers typically include about 1 to about 20 alkoxy groups, for example, about 2 to about 10, about 3 to about 8, and/or about 4 to about 6 alkoxy groups. Alkoxy groups include, but are not limited to: methoxy groups, ethoxy groups, and propoxy groups.

Alkyl and alkenyl multifunctional acrylic monomers typically comprise about 4 to about 40 carbon atoms, for example, about 5 to about 21, about 6 to about 18, and/or about 7 to about 15 carbon atoms. The alkyl and alkenyl multifunctional acrylic monomers also can comprise more than 40 carbon atoms. Heterocyclic multifunctional acrylic monomers typically comprise about 5 to about 40 carbon atoms, and one or more heteroatoms such as N, O, or S.

Exemplary multifunctional acrylic monomers include, but are not limited to: 1,12-dodecanediol diacrylate, 1,12-dodecanediol dimethacrylate, 1,3-butylene glycol diacrylate, 1,3-butylene glycol dimethacrylate, 1,4-butanediol diacrylate, 1,4-butanediol dimethacrylate, 1,6-hexanediol diacrylate, 1,6-hexanediol dimethacrylate, alkoxylated cyclohexane dimethanol diacrylates, alkoxylated cyclohexane dimethanol dimethacrylates, alkoxylated hexanediol diacrylates, alkoxylated hexanediol dimethacrylates, alkoxylated neopentyl glycol diacrylates, alkoxylated neopentyl glycol dimethacrylates, cyclohexane dimethanol diacrylate, cyclohexane dimethanol dimethacrylate, diethylene glycol diacrylate, diethylene glycol dimethacrylate, dipropylene glycol diacrylate, dipropylene glycol dimethacrylate, ethoxylated bisphenol A diacrylates, ethoxylated bisphenol A dimethacrylates, ethylene glycol diacrylate, ethylene glycol dimethacrylate, neopentyl glycol diacrylate, neopentyl glycol dimethacrylate, polyethylene glycol diacrylates, polyethylene glycol dimethacrylates, propylene glycol diacrylates, propylene glycol dimethacrylates, propoxylated neopentyl glycol diacrylates, propoxylated neopentyl glycol dimethacrylates, tetraethylene glycol diacrylate, tetraethylene glycol dimethacrylate, triethylene glycol diacrylate, triethylene glycol dimethacrylate, tripropylene glycol diacrylate, tripropylene glycol dimethacrylate, ethoxylated trimethylolpropane triacrylates, ethoxylated trimethylolpropane trimethacrylates, propoxylated glyceryl triacrylates, propoxylated glyceryl trimethacrylates, trimethylolpropane triacrylate, trimethylolpropane trimethacrylate, pentaerythritol triacrylate, pentaerythritol trimethacrylate, propoxylated trimethylolpropane triacrylates, propoxylated trimethylolpropane trimethacrylates, tris(2-hydroxyethyl)isocyanurate triacrylate, tris(2-hydroxyethyl)isocyanurate trimethacrylate, di-trimethylolpropane tetraacrylate, dipentaerythritol pentaacrylate, ethoxylated pentaerythritol tetraacrylates, dipentaerythritol pentaacrylate, pentaerythritol tetraacrylate, and mixtures of the foregoing.

Preferred multifunctional acrylic monomers include 1,3-butylene glycol diacrylate, 1,4-butanediol diacrylate, 1,6-hexanediol diacrylate, and mixtures of the foregoing.

In some embodiments, the multifunctional acrylic monomer and the adhesion-promoting acrylic monomer can be the same.

Adhesion-Promoting Acrylic or Vinyl Monomers

Antimicrobial resin compositions in accordance with the present disclosure are prepared from a mixture comprising about 5 weight % to about 40 weight % of an adhesion-promoting acrylic monomer. Suitable ranges include, but are not limited to, about 10 weight % to about 35 weight %, and/or about 15 weight % to about 30 weight %. The mixture can comprise, for example, about 5 weight % to about 10 weight %, about 10 weight % to about 15 weight %, about 15 weight % to about 20 weight %, about 20 weight % to about 25 weight %, about 25 weight % to about 30 weight %, about 30 weight % to about 35 weight %, and/or about 35 weight % to about 40 weight % of the adhesion-promoting acrylic monomer. Mixtures including more than one adhesion-promoting acrylic monomer also can be used.

In accordance with the present disclosure, the adhesion-promoting acrylic monomer can comprise acrylate esters, methacrylate esters, acrylamides, methacrylamides, or mixtures of the foregoing. The adhesion-promoting acrylic monomers can be monofunctional monomers (i.e., monomers having one acrylate, methacrylate, acrylamide, or methacrylamide group). The adhesion-promoting acrylic monomers also can be difunctional monomers, trifunctional monomers, tetrafunctional monomers, pentafunctional monomers, hexafunctional monomers, or mixtures of the foregoing. Adhesion-promoting acrylic monomers having more than one functional group can comprise the same functional groups or different functional groups. A difunctional adhesion-promoting acrylic monomer, for example, can comprise one acrylate group and one methacrylamide group. A difunctional adhesion-promoting acrylic monomer also can comprise, for example, two methacrylate groups. Adhesion-promoting acrylic monomers having more than six functional groups (e.g., eight or ten functional groups) and mixtures of the foregoing adhesion-promoting acrylic monomer s also can be used.

In some embodiments, the adhesion-promoting acrylic monomer can be the same as the multifunctional acrylic monomer.

Adhesion-promoting acrylic or vinyl monomers can be hydrophilic or hydrophobic. Hydrophilic monomers can advantageously provide increased hydrophilicity to the resin composition. Suitable hydrophilic monomers can comprise, for example, pendent hydrophilic groups such as alcohols, amines, thiols, carboxylates, phosphates, and sulfates. Exemplary hydrophilic monomers include, but are not limited to, 1,3-butylene glycol diacrylate, 1,3-butylene glycol dimethacrylate, 1,4-butanediol diacrylate, 1,4-butanediol dimethacrylate, 1,6-hexanediol diacrylate, 1,6-hexanediol dimethacrylate, 2-hydroxyethyl acrylate, 2-hydroxyethyl methacrylate, 4-hydroxybutyl acrylate, 4-hydroxybutyl methacrylate, and 2-(2-ethoxyethoxy)ethyl acrylate.

Suitable adhesion-promoting acrylic monomers include, but are not limited to: alkoxylated acrylates; alkoxylated methacrylates; linear, branched, or cyclic alkyl acrylates; linear, branched, or cyclic alkyl methacrylates; linear, branched, or cyclic alkyl acrylamides; linear, branched, or cyclic alkyl methacrylamides; linear, branched, or cyclic alkenyl acrylates; linear, branched, or cyclic alkenyl methacrylates; linear, branched, or cyclic alkenyl acrylamides; linear, branched, or cyclic alkenyl methacrylamides; alkoxylated linear, branched, or cyclic alkyl acrylates; alkoxylated linear, branched, or cyclic alkyl methacrylates; alkoxylated linear, branched, or cyclic alkenyl acrylates; alkoxylated linear, branched, or cyclic alkenyl methacrylates; heterocyclic acrylates; heterocyclic methacrylates; heterocyclic acrylamides; heterocyclic methacrylamides; caprolactone acrylates; caprolactone methacrylates; caprolactam acrylamides; caprolactam methacrylamides; valerolactone acrylates; valerolactone methacrylates; valerolactam acrylamides; valerolactam methacrylamides; butyrolactone acrylates; butyrolactone methacrylates; butyrolactam acrylamides; butyrolactam methacrylamides; propiolactone acrylates; propiolactone methacrylates; propiolactam acrylamides; propiolactam methacrylamides; acrylic acid; and mixtures of the foregoing. Monofunctional, difunctional, trifunctional, tetrafunctional, pentafunctional, and hexafunctional derivatives of the foregoing also are included.

Alkoxylated adhesion-promoting acrylic monomers typically include about 1 to about 20 alkoxy groups, for example, about 2 to about 10, about 3 to about 8, and/or about 4 to about 6 alkoxy groups. Alkoxy groups include, but are not limited to: methoxy groups, ethoxy groups, and propoxy groups.

Alkyl and alkenyl adhesion-promoting acrylic monomers typically comprise about 4 to about 40 carbon atoms, for example, about 5 to about 21, about 6 to about 18, and/or about 7 to about 15 carbon atoms. The alkyl and alkenyl adhesion-promoting acrylic monomers also can comprise more than 40 carbon atoms. Heterocyclic adhesion-promoting acrylic monomers typically comprise about 5 to about 40 carbon atoms, and one or more heteroatoms such as N, O, or S.

Caprolactone, valerolactone, butyrolactone, and propiolactone acrylate monomers typically comprise about 1 to about 10 caprolactone, valerolactone, butyrolactone, or propiolactone groups, for example, about 2 to about 8 and/or about 3 to about 6 groups. Caprolactam, valerolactam, butyrolactam, and propiolactam acrylamide monomers typically comprise about 1 to about 10 caprolactam, valerolactam, butyrolactam, or propiolactam groups, for example, about 2 to about 8 and/or about 3 to about 6 groups.

Exemplary adhesion-promoting acrylic monomers include, but are not limited to: acrylic acid, methacrylic acid, 2-(2-ethoxyethoxy)ethyl acrylate, 2-(2-ethoxyethoxy)ethyl methacrylate, 2-phenoxyethyl acrylate, 2-phenoxyethyl methacrylate, 3,3,5-trimethylcyclohexyl acrylate, 3,3,5-trimethylcyclohexyl methacrylate, alkoxylated lauryl acrylates, alkoxylated lauryl methacrylates, alkoxylated phenol acrylates, alkoxylated phenol methacrylates, alkoxylated tetrahydrofurfuryl acrylates, alkoxylated tetrahydrofurfuryl methacrylates, lauryl acrylate, lauryl methacrylate, cyclic trimethylolpropane formal acrylate, cyclic trimethylolpropane formal methacrylate, dicyclopentadienyl acrylate, dicyclopentadienyl methacrylate, diethylene glycol methyl ether acrylate, diethylene glycol methyl ether methacrylate, ethoxylated hydroxyethyl acrylates, ethoxylated hydroxyethyl methacrylates, ethoxylated nonyl phenol acrylates, ethoxylated nonyl phenol methacrylates, isobornyl acrylate, isobornyl methacrylate, isodecyl acrylate, isodecyl methacrylate, isoocyl acrylate, isoocyl methacrylate, metallic acrylates, metallic methacrylates, methoxy polyethylene glycol acrylates, methoxy polyethylene glycol methacrylates, octyldecyl acrylate, octyldecyl methacrylate, polypropylene glycol acrylates, polypropylene glycol methacrylates, propoxylated allyl acrylates, propoxylated allyl methacrylates, stearyl acrylate, stearyl methacrylate, tetrahydrofurfuryl acrylate, tetrahydrofurfuryl methacrylate, tridecyl acrylate, tridecyl methacrylate, triethylene glycol ethyl ether acrylate, triethylene glycol ethyl ether methacrylate, 1,12-dodecanediol diacrylate, 1,12-dodecanediol dimethacrylate, 1,3-butylene glycol diacrylate, 1,3-butylene glycol dimethacrylate, 1,4-butanediol diacrylate, 1,4-butanediol dimethacrylate, 1,6-hexanediol diacrylate, 1,6-hexanediol dimethacrylate, alkoxylated cyclohexane dimethanol diacrylates, alkoxylated cyclohexane dimethanol dimethacrylates, alkoxylated hexanediol diacrylates, alkoxylated hexanediol dimethacrylates, alkoxylated neopentyl glycol diacrylates, alkoxylated neopentyl glycol dimethacrylates, cyclohexane dimethanol diacrylate, cyclohexane dimethanol dimethacrylate, diethylene glycol diacrylate, diethylene glycol dimethacrylate, dipropylene glycol diacrylate, dipropylene glycol dimethacrylate, ethoxylated bisphenol A diacrylates, ethoxylated bisphenol A dimethacrylates, ethylene glycol diacrylate, ethylene glycol dimethacrylate, neopentyl glycol diacrylate, neopentyl glycol dimethacrylate, polyethylene glycol diacrylates, polyethylene glycol dimethacrylates, propylene glycol diacrylates, propylene glycol dimethacrylates, propoxylated neopentyl glycol diacrylates, propoxylated neopentyl glycol dimethacrylates, tetraethylene glycol diacrylate, tetraethylene glycol dimethacrylate, triethylene glycol diacrylate, triethylene glycol dimethacrylate, tripropylene glycol diacrylate, tripropylene glycol dimethacrylate, ethoxylated trimethylolpropane triacrylates, ethoxylated trimethylolpropane trimethacrylates, propoxylated glyceryl triacrylates, propoxylated glyceryl trimethacrylates, trimethylolpropane triacrylate, trimethylolpropane trimethacrylate, pentaerythritol triacrylate, pentaerythritol trimethacrylate, propoxylated trimethylolpropane triacrylates, propoxylated trimethylolpropane trimethacrylates, tris(2-hydroxyethyl)isocyanurate triacrylate, tris(2-hydroxyethyl)isocyanurate trimethacrylate, di-trimethylolpropane tetraacrylate, dipentaerythritol pentaacrylate, ethoxylated pentaerythritol tetraacrylates, dipentaerythritol pentaacrylate, pentaerythritol tetraacrylate, and mixtures of the foregoing.

Exemplary adhesion-promoting acrylic monomers also include, but are not limited to: 3,3,5-trimethylcyclohexyl acrylamide, 3,3,5-trimethylcyclohexyl methacrylamide, dicyclopentadienyl acrylamide, dicyclopentadienyl methacrylamide, isobornyl acrylamide, isobornyl methacrylamide, isodecyl acrylamide, isodecyl methacrylamide, isoocyl acrylamide, isoocyl methacrylamide, octyldecyl acrylamide, octyldecyl methacrylamide, stearyl acrylamide, stearyl methacrylamide, tetrahydrofurfuryl acrylamide, tetrahydrofurfuryl methacrylamide, tridecyl acrylamide, tridecyl methacrylamide, dimethyl acrylamide, dimethyl methacrylamide, and mixtures of the foregoing.

Preferred adhesion-promoting acrylic monomers include acrylic acid, N,N-dimethyl acrylamide, 1,3-butylene glycol diacrylate, 1,4-butanediol diacrylate, 1,6-hexanediol diacrylate, 2-hydroxyethyl methacrylate, 4-hydroxybutyl acrylate, tetrahydrofurfuryl acrylate, 2-(2-ethoxyethoxy)ethyl acrylate, and mixtures of the foregoing.

Adhesion-promoting vinyl monomers include, for example, N-vinyl pyrrolidone.

Antimicrobial Metal Salts

Antimicrobial resin compositions in accordance with the present disclosure are prepared from a mixture comprising about 0.1 weight % to about 15 weight % of an antimicrobial metal salt. Suitable ranges include, but are not limited to, about 0.5 weight % to about 10 weight %, and/or about 1 weight % to about 8 weight %. The mixture can comprise, for example, about 0.1 weight % to about 1 weight %, about 1 weight % to about 5 weight %, about 5 weight % to about 10 weight %, and/or about 10 weight % to about 15 weight % of the metal salt. Mixtures including more than one metal salt also can be used.

In accordance with the present disclosure, the antimicrobial metal salt can comprise metal salts including, but not limited to, salts of silver, copper, gold, zinc, cerium, platinum, palladium, tin, and mixtures of the foregoing. Mixtures of metals salts also can be used. Suitable metal salts include, but are not limited to metal sulfadiazines, metal halides (e.g., metal fluorides, metal chlorides, metal bromides, metal iodides), metal acetates, metal hydroxides, metal carbonates, metal oxalates, metal phosphates, metal sulfates, metal chlorates, metal bromates, metal iodates, and mixtures of the foregoing. Exemplary metal salts include, but are not limited to, silver salts, such as silver sulfadiazine, silver halides (e.g., silver fluoride, silver chloride, silver bromide, silver iodide), silver acetate, silver hydroxide, silver carbonate, silver oxalate, silver phosphate, silver sulfate, silver chlorate, silver bromate, silver iodate, and mixtures of the foregoing.

The metal salt in accordance with the present disclosure can comprise particles, such as microparticles or nanoparticles. The metal salt particles typically have a diameter in the range of about 1 nanometer to about 50 micrometers, for example, from about 10 nanometers to about 25 micrometers, from about 50 nanometers to about 10 micrometers, and/or from about 100 nm to about 1 micrometer.

Initiators

Antimicrobial resin compositions in accordance with the present disclosure optionally can be prepared from a mixture comprising about 0.1 weight % to about 15 weight % of an initiator. Suitable ranges include, but are not limited to, about 0.5 weight % to about 10 weight %, and/or about 1 weight % to about 8 weight %. The mixture can comprise, for example, about 0.1 weight % to about 1 weight %, about 1 weight % to about 5 weight %, about 5 weight % to about 10 weight %, and/or about 10 weight % to about 15 weight % of the initiator. Mixtures including more than initiator also can be used.

Suitable initiators include, but are not limited to: α-hydroxyketones, phenylglyoxylates, benzyldimethyl ketals, α-aminoketones, mono acyl phosphines, bis acyl phosphines, phosphine oxides, metallocenes (e.g., fluorinated diaryl titanocenes such as IRGACURE® 784), iodonium salts, mercaptobenzothiazoles, mercptobenzooxazoles, benzophenones, acetophenones, benzoin alkyl ethers, hexaarylbisimidazoles, and mixtures thereof.

Exemplary photoinitiators include, but are not limited to: 1-hydroxycyclohexyl phenyl ketone, benzophenone, 2-hydroxy-2-methyl-1-phenyl-1-propanone, 2-hydroxy-1-[4-(2-hydroxyethoxy)phenyl]-2-methyl-1-propanone, methylbenzoylformate, oxy-phenyl-acetic acid 2-[2-oxo-2-phenyl-acetoxy-ethoxy]-ethyl ester, oxy-phenyl-acetic acid 2-[2-hydroxy-ethoxy]-ethyl ester, α,α-dimethoxy-α-phenylacetophenone, 2-benzyl-2-(dimethylamino)-1-[4-(4-morpholinyl)phenyl]-1-butanone, 2-methyl-1-[4-(methylthio)phenyl]-2-(4-morpholinyl)-1-propanone, diphenyl (2,4,6-trimethylbenzoyl)-phosphine oxide, phenyl bis(2,4,6-trimethyl benzoyl)phosphine oxide, bis($\eta^5$-2,4-cyclopentadien-1-yl)bis[2,6-difluoro-3-(1H-pyrrol-1-yl)phenyl]titanium, (4-methylphenyl)-[4-(2-methylpropyl)phenyl]-iodonium hexafluorophosphate, 2,2-dimethoxy-1,2-diphenylethan-1-one, 2,4,6-trimethylbenzoyldiphenylphosphine oxide (LUCIRIN TPO®), and mixtures of the foregoing.

Additional suitable initiators include, but are not limited to: azobisbutyronitrile and dibenzoyl peroxides.

Additives

The antimicrobial resin formulations optionally comprise one or more additives. Suitable additives include, but are not limited to: photoinitiators (e.g., benzophenone and pyruvic acid), stabilizers, chain transfer agents, plasticizers, light stabilizers, UV screening compounds, leveling agents, wetting agents, preservatives, adhesion promoters, emulsifiers, pigments, dyes (e.g., eosin, methylene blue, and ketocumarines), or fillers. The optional additives typically comprise about 0.1 weight % to about 20 weight % of the formulations, for example, about 0.5 weight % to about 15 weight %, about 1 weight % to about 10 weight %, and/or about 2 weight % to about 5 weight %.

The additive can comprise saturated fatty acids, unsaturated fatty acids, or mixtures thereof. Fatty acids can advantageously stabilize silver salt dispersions, thereby maintaining the silver salt in a highly dispersed state during the curing step. Suitable fatty acids include, but are not limited to: decanoic acid, lauric acid, myristic acid, palmitic acid, stearic acid, eicosanoic acid, docsanoic acid, tetracosanoic acid, α-linolenic acid, stearidonic acid, eicosapentaenoic acid, docosahexaenoic acid, linoleic acid, γ-linolenic acid, dihomo-γ-linolenic acid, arachidonic acid, oleic acid, erucic acid, nervonic acid, or mixtures of the foregoing. Quaternary ammonium compounds also can provide stabilization of silver salt dispersions.

Suitable fillers for the formulations according to the disclosure include, for example, polymers soluble in the reactive acrylic monomers, such as polyvinyl alcohol and polyvinyl butyrate.

Antimicrobial Resins

The antimicrobial resins of the present disclosure are formed by providing a mixture comprising one or more hydrophilic acrylic oligomers, one or more multifunctional acrylic monomers, one or more adhesion-promoting acrylic or vinyl monomers, and one or more antimicrobial metal salts; and exposing the mixture to a radiation source. Exposure of the mixture to the radiation source cures at least a portion of the mixture. Combining the aforementioned components and exposing same to radiation provides more efficacious antimicrobial resins, as previously discussed. Additionally, the components have been selected so that the formed resin is hydrophilic and has hydrogel-like properties such that it is compatible with biological tissues. Hydrophilicity advantageously can promote continuous and rapid release of the antimicrobial metal salt from the resin into aqueous solution. Furthermore, the antimicrobial resins of the present disclosure comprise components that advantageously promote the stabilization of metal salt dispersions, thereby facilitating the preparation of more homogeneously dispersed resins comprising difficult to disperse metal salts (e.g., silver sulfadiazine). As previously discussed, more homogeneously dispersed metal salts can have improved efficacy and/or more desirable elution profiles.

The radiation source can comprise an ultraviolet (UV) light source, an electron beam source, a gamma radiation source, a X-ray source, an ion beam source, a microwave source, a heat source, or a combination of the foregoing. Generally where electron beam radiation is used, the amount can be from about 1 to about 10 Mrads, for example, from about 3 to about 8 Mrads. Where a UV light source is used, the radiation amount can be from about 0.1 J/cm² to about 5 J/cm².

In accordance with the methods of the present disclosure, the antimicrobial resins can be formed on a substrate surface by providing a mixture comprising one or more hydrophilic acrylic oligomers, one or more multifunctional acrylic monomers, one or more adhesion-promoting acrylic or vinyl monomers, and one or more metal salts, providing the mixture on the substrate surface, and exposing the mixture to a radiation source. The mixture can be provided on the substrate surface by various manual and mechanical means of application, for example, by spreading, layering, dipping, coating, swabbing, spraying, pouring, and/or washing. Prior to providing the mixture on the substrate surface, the mixture typically has a viscosity of about 50 centipoise (cP) to about 1000 cP, for example, about 100 cP to about 800 cP, about 200 cP to about 600 cP, and/or about 300 cP to about 500 cP, but higher and lower viscosities also can be used.

The antimicrobial resins in accordance with the present disclosure comprise about 15 weight % to about 80 weight % of hydrophilic acrylic oligomer units, about 10 weight % to about 80 weight % of multifunctional acrylic monomer units, about 5 weight % to about 40 weight % of adhesion-promoting acrylic or vinyl monomer units, and about 0.1 weight % to about 15 weight % of an antimicrobial metal salt. The hydrophilic acrylic oligomer units, the multifunctional acrylic monomer units, and the adhesion-promoting acrylic or vinyl monomer units of the antimicrobial resins are typically substantially cured, or cross-linked, after exposure to radiation.

The present disclosure also is directed to an antimicrobial resin composition prepared by a process comprising: providing a mixture comprising about 15 weight % to about 80 weight % of a hydrophilic acrylic oligomer, about 10 weight % to about 80 weight % of a multifunctional acrylic monomer, about 5 weight % to about 40 weight % of an adhesion-promoting acrylic or vinyl monomer, and about 0.1 weight % to about 15 weight % of an antimicrobial metal salt; and exposing the mixture to a radiation source to cure at least a portion of the mixture, thereby forming an antimicrobial resin.

The disclosure may be better understood by reference to the following examples which are not intended to be limiting, but rather only set forth exemplary embodiments in accordance with the disclosure.

EXAMPLES

Example 1

Preparation of Antimicrobial Resins on Polycarbonate Surfaces

An antimicrobial resin was prepared by combining SR 610 polyethylene glycol diacrylate (23.63 weight %), CD9038 ethoxylated bisphenol A diacrylate (28.35 weight %), acrylic acid (9.45 weight %), dimethyl acrylamide (9.45 weight %), SR 238 hexanediol diacrylate (9.45 weight %), 2-hydroxyethyl methacrylate (9.45 weight %), stearic acid (0.50 weight %), and silver sulfadiazine (5.00 weight %). IRGACURE® 651 α,α-dimethoxy-α-phenylacetophenone initiator (4.72 weight %) was added, and the resulting mixture was applied to a polycarbonate surface. The polycarbonate surface was then exposed to a UV light source (approximately 0.5 J/cm²) to cure the mixture, thereby forming a coating comprising an antimicrobial resin on the polycarbonate surface. The cured antimicrobial resin adhered strongly to the polycarbonate surface.

| Component | Weight % | Function | Supplier |
|---|---|---|---|
| IRGACURE ® 651 (α,α-dimethoxy-α-phenylacetophenone) | 4.72 | Initiator | Ciba |
| SR 610 (polyethylene glycol-600 diacrylate) | 23.63 | Oligomer/monomer | Sartomer |
| CD 9038 (30 mole ethoxylated bisphenol A diacrylate) | 28.35 | Oligomer | Sartomer |
| Acrylic acid | 9.45 | Monomer | Aldrich |

-continued

| Component | Weight % | Function | Supplier |
|---|---|---|---|
| Dimethyl acrylamide | 9.45 | Monomer | Aldrich |
| SR 238 (1,6-hexanediol diacrylate) | 9.45 | Monomer | Sartomer |
| 2-Hydroxyethyl methacrylate | 9.45 | Monomer | Aldrich |
| Silver sulfadiazine | 5.00 | Antimicrobial agent | Aldrich |
| Stearic acid | 0.50 | Emulsifier | Aldrich |

The antimicrobial resin formed after UV curing was observed to be hydrophilic, and rapidly increased in weight due to the absorption of water (data not shown). Hydrophilicity advantageously can promote continuous and rapid release of the antimicrobial metal salt from the resin into aqueous solution.

Figure 2:
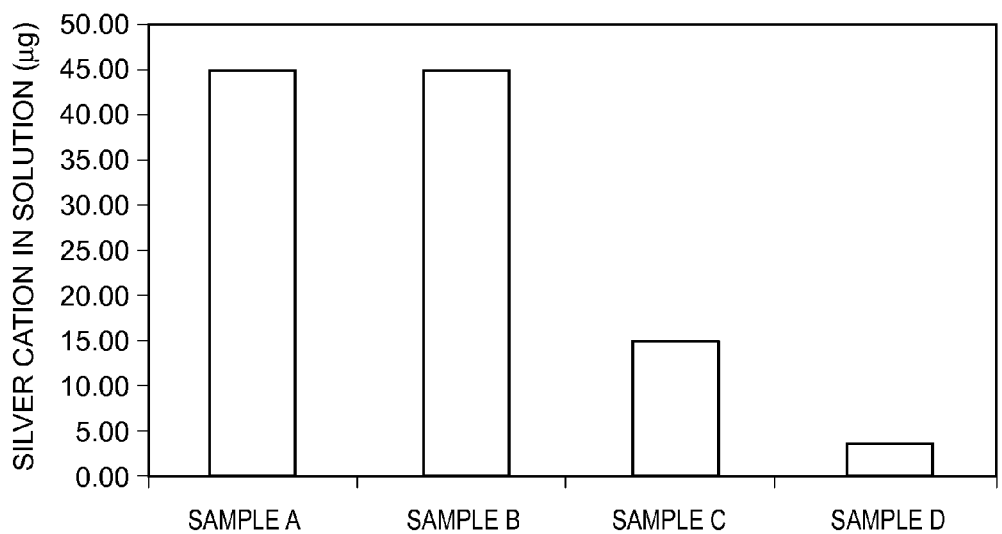
FIG. 2 is a graph showing the total amount of silver released from the samples of FIG. 1 after 96 hours.

The elution profile of silver ions released from the antimicrobial resin was tested by placing the polycarbonate surface carrying the antimicrobial resin in aqueous solution and detecting silver ion levels. An initial burst of silver ions was released within approximately 30 minutes of the start of the measurements. After the initial burst, the release of silver ions declined slightly, stabilizing at about 50 minutes after the start of the experiment (see FIG. 1, Sample B) and providing sustained release of a relatively high concentration of silver for at least 48 hours. High total amounts of silver ion were released over 96 hours by the antimicrobial resin prepared in accordance with the disclosed methods (see FIG. 2, Sample B). In contrast, coatings of approximately the same thicknesses prepared from formulations not in accordance with the disclosure released lower overall levels of silver (see FIG. 2, Samples C and D), and did not exhibit sustained release of a relatively high concentration of silver ions (see FIG. 1, Samples A, C, and D). The coating of comparative Sample A included a silver-containing polyvinyl alcohol hydrogel layer prepared in accordance with the disclosure of U.S. Patent Publication No. 2008/0063693. The coating of comparative Sample C included silver nanoparticles and a stabilizing agent and was prepared in accordance with the disclosure of U.S. Patent Publication No. 2007/0003603. The coating of comparative Sample D was prepared by blending 8% ALPHA-SAN® antimicrobial silver additive (available from Milliken & Company, Spartanburg, S.C.) in MAKROLON® Rx-1805 medical grade polycarbonate resin (available from Bayer Materials Science, Pittsburgh, Pa.) and applying the coating to a substrate surface.

Example 2

Antimicrobial Activity of Radiation-Cured Resins

The antimicrobial resin-carrying polycarbonate surface prepared in Example 1 was tested to determine its ability to inhibit growth of microorganisms. Polycarbonate surfaces carrying coatings comprising antimicrobial resins not in accordance with the disclosure (see Example 1) and an uncoated polycarbonate surface were also tested. A suspension of Staphylococcus aureus (S. aureus) was grown in tryptic soy broth for 18-24 hours. The suspension was then diluted in saline to $6.4 \times 10^5$ colony-forming units per mL (cfu/mL). Tubes containing 5 mL saline were inoculated with 0.1 mL ($6.4 \times 10^4$ cfu) of the suspension. Samples A-D and an uncoated polycarbonate surface were aseptically added to the tubes, which were incubated at 20-25° C. for 48 hours. The samples then were plated in tryptic soy agar in triplicate and incubated at 30-35° C. for 48 hours. After this time, growth of S. aureus was measured, as shown in FIG. 3. The antimicrobial resin prepared in accordance with the disclosure (see FIG. 3, Sample B) displayed about 10-fold improved antimicrobial activity 96 hours after treatment with S. aureus, compared to the antimicrobial resins not prepared in accordance with the disclosed methods (see FIG. 3, Samples A, C and D) and the uncoated polycarbonate surface (see FIG. 3, Control).

What is claimed is:

1. A method for forming an antimicrobial resin comprising:
providing a mixture comprising about 15 weight % to about 80 weight % of a hydrophilic acrylic oligomer, about 10 weight % to about 80 weight % of a multifunctional acrylic monomer, about 5 weight % to about 40 weight % of a monofunctional adhesion-promoting acrylic or vinyl monomer, and about 0.1 weight % to about 15 weight % of an antimicrobial metal salt; and
exposing the mixture to a radiation source to cure at least a portion of the mixture, thereby forming an antimicrobial resin.

2. The method of claim 1, further comprising forming a medical device or medical device component comprising the antimicrobial resin.

3. The method of claim 1, further comprising applying the antimicrobial resin to a substrate surface to form a coating on the substrate surface.

4. The method of claim 1, further comprising forming a coating comprising:
providing the mixture on a substrate surface before exposing the mixture to the radiation source.

5. The method of claim 4, wherein the substrate surface comprises at least one plastic, glass, metal, ceramic, elastomer, or mixtures or laminates thereof.

6. The method of claim 4, wherein the substrate surface comprises a plastic or elastomer selected from the group consisting of acrylonitrile butadiene styrenes, polyamides, polycarbonates, polyesters, polyetheretherketones, polyetherimides, polyethylenes, polyethylene terephthalates, polylactic acids, polymethyl methyacrylates, polypropylenes, polystyrenes, polyurethanes, poly(vinyl chlorides), polyvinylidene chlorides, polyethers, polysulfones, silicones, natural rubbers, synthetic rubbers, styrene butadiene rubbers, ethylene propylene diene monomer rubbers, polychloroprene rubbers, acrylonitrile butadiene rubbers, chlorosuphonated polyethylene rubbers, polyisoprene rubbers, isobutylene-isoprene copolymeric rubbers, chlorinated isobutylene-isoprene copolymeric rubbers, brominated isobutylene-isoprene copolymeric rubbers, and mixtures and copolymers thereof.

7. The method of claim 4, wherein the substrate surface comprises a surface of a medical device or medical device component.

8. The method of claim 4, wherein the substrate surface comprises a surface of a medical fluid container or medical fluid flow system.

9. The method of claim 4, wherein the substrate surface comprises a surface of an I.V. set.

10. The method of claim 4, wherein the substrate surface comprises a surface of a medical device or medical device component selected from the group consisting of: I.V. tubing, I.V. fluid bags, access devices for I.V. sets, septa, stopcocks, I.V. set connectors, I.V. set adaptors, clamps, I.V. filters, catheters, needles, and cannulae.

11. The method of claim 4, wherein the substrate surface comprises a surface of a luer access device or a needleless luer access device.

12. The method of claim 4, wherein the radiation source comprises an ultraviolet (UV) light source, an electron beam source, a gamma radiation source, an X-ray source, an ion beam source, a microwave source, a heat source, or a combination of the foregoing.

13. The method of claim 4, wherein the hydrophilic acrylic oligomer comprises monofunctional oligomers, difunctional oligomers, trifunctional oligomers, tetrafunctional oligomers, pentafunctional oligomers, hexafunctional oligomers, or mixtures thereof.

14. The method of claim 4, wherein the hydrophilic acrylic oligomer comprises polyepoxy acrylates, polyurethane acrylates, polyester acrylates, polyether acrylates, amine-modified polyether acrylates, polyacrylic acrylates, polycarbonate acrylates, polyepoxy methacrylates, polyurethane methacrylates, polyester methacrylates, polyether methacrylates, amine-modified polyether methacrylates, polyacrylic methacrylates, polycarbonate methacrylates, polyepoxy acrylamides, polyurethane acrylamides, polyester acrylamides, polyether acrylamides, amine-modified polyether acrylamides, polyacrylic acrylamides, polycarbonate acrylamides, polyepoxy methacrylamides, polyurethane methacrylamides, polyester methacrylamides, polyether methacrylamides, amine-modified polyether methacrylamides, polyacrylic methacrylamides, polycarbonate methacrylamides, or mixtures thereof.

15. The method of claim 4, wherein the hydrophilic acrylic oligomer comprises ethoxylated bisphenol A diacrylates, polyethylene glycol diacrylates, or mixtures thereof.

16. The method of claim 4, wherein the multifunctional acrylic monomer comprises acrylate esters, methacrylate esters, acrylamides, methacrylamides, or mixtures thereof.

17. The method of claim 4, wherein the multifunctional acrylic monomer comprises difunctional monomers, trifunctional monomers, tetrafunctional monomers, pentafunctional monomers, hexafunctional monomers, or mixtures thereof.

18. The method of claim 4, wherein the multifunctional acrylic monomer comprises 1,3-butylene glycol diacrylate, 1,4-butanediol diacrylate, 1,6-hexanediol diacrylate, or mixtures thereof.

19. The method of claim 4, wherein the monofunctional adhesion-promoting acrylic or vinyl monomer comprises acrylate esters, methacrylate esters, acrylamides, methacrylamides, or mixtures thereof.

20. The method of claim 4, wherein the monofunctional adhesion-promoting acrylic or vinyl monomer comprises acrylic acid, N,N-dimethyl acrylamide, 2-hydroxyethyl methacrylate, 4-hydroxybutyl acrylate, tetrahydrofurfuryl acrylate, 2-(2-ethoxyethoxy)ethyl acrylate, N-vinyl pyrrolidone, or mixtures thereof.

21. The method of claim 4, wherein the metal salt comprises a metal selected from the group consisting of silver, copper, gold, zinc, cerium, and mixtures thereof.

22. The method of claim 4, wherein the metal salt comprises silver.

23. The method of claim 4, wherein the metal salt comprises silver sulfadiazine.

24. The method of claim 4, wherein the metal salt comprises particles having a diameter of about 1 nanometer to about 50 micrometers.

25. The method of claim 4, wherein the metal salt comprises silver sulfadiazine particles.

26. The method of claim 4, wherein the mixture further comprises about 0.1 weight % to about 15 weight % of an initiator.

27. The method of claim 26, wherein the initiator comprises α-hydroxyketones, phenylglyoxylates, benzyldimethyl ketals, α-aminoketones, mono acyl phosphines, bis acyl phosphines, phosphine oxides, metallocenes, iodonium salts, mercaptobenzothiazoles, mercaptobenzooxazoles, benzophenones, acetophenones, benzoin alkyl ethers, hexaarylbisimidazoles, and mixtures thereof.

28. The method of claim 26, wherein the initiator comprises 2,2-dimethoxy-1,2-diphenylethan-1-one, 2,4,6-trimethylbenzoyldiphenylphosphine oxide, or mixtures thereof.

29. The method of claim 4, wherein the mixture further comprises a saturated fatty acid, an unsaturated fatty acid, or a mixture thereof.

30. The method of claim 4, wherein the mixture further comprises a fatty acid selected from the group consisting of: decanoic acid, lauric acid, myristic acid, palmitic acid, stearic acid, eicosanoic acid, docsanoic acid, tetracosanoic acid, α-linolenic acid, stearidonic acid, eicosapentaenoic acid, docosahexaenoic acid, linoleic acid, γ-linolenic acid, dihomo-γ-linolenic acid, arachidonic acid, oleic acid, erucic acid, nervonic acid, and mixtures thereof.

31. The method of claim 1, wherein hydrophilic acrylic oligomer is selected from the group consisting of difunctional oligomers, trifunctional oligomers, tetrafunctional oligomers, pentafunctional oligomers, hexafunctional oligomers, or mixtures thereof, and wherein the multifunctional acrylic monomer is selected from the group consisting of alkyl multifunctional monomers and alkenyl multifunctional monomers.

* * * * *